United States Patent [19]

Riese et al.

[11] Patent Number: 4,736,314

[45] Date of Patent: Apr. 5, 1988

[54] MEASURING THE CONTENT OF CRYSTALS

[75] Inventors: Hans Riese, Lund; Christer Göransson, Malmö, both of Sweden

[73] Assignee: Alfa-Laval Food & Dairy Engineering AB, Lund, Sweden

[21] Appl. No.: 893,306

[22] PCT Filed: Nov. 14, 1985

[86] PCT No.: PCT/SE85/00454

§ 371 Date: Jun. 27, 1986

§ 102(e) Date: Jun. 27, 1986

[87] PCT Pub. No.: WO86/03298

PCT Pub. Date: Jun. 5, 1986

[30] Foreign Application Priority Data

Nov. 19, 1984 [SE] Sweden ............... 8405782

[51] Int. Cl.⁴ ................. C12G 3/00; G06F 15/32
[52] U.S. Cl. ................. 364/564; 364/524; 374/101; 426/524
[58] Field of Search ............... 374/101, 160; 426/330.4, 15; 364/509, 564

[56] References Cited

U.S. PATENT DOCUMENTS

| | | | |
|---|---|---|---|
| 2,658,383 | 11/1953 | Chipley | 374/16 |
| 2,750,433 | 6/1956 | Le Tourneau et al. | 374/16 X |
| 3,205,699 | 9/1965 | Van Assendelft | 374/16 |
| 4,015,020 | 3/1977 | Nagasawa et al. | 426/15 X |
| 4,112,128 | 9/1978 | Oessler | 426/330.4 |
| 4,322,446 | 3/1982 | Heess et al. | 426/330.4 |
| 4,351,851 | 9/1982 | Riese | 165/65 X |

*Primary Examiner*—Daniel M. Yasich
*Attorney, Agent, or Firm*—Davis Hoxie Faithfull & Hapgood

[57] ABSTRACT

An arrangement for measuring the content of crystals in a mixture of liquid and crystals comprises a pipe line (2) and a pump (5), by which a constant flow of the mixture is pumped through the pipe line (2). In this, a unit (6), preferably an electrical resistance wire, is arranged to transmit a constant amount of heat to the flow. There are also temperature sensors (7, 8) before and after the unit (6), arranged to transmit impulses representing the temperature difference to a unit (11), which with the aid of information about the velocity of the flow, the added amount of heat, the specific heat of the liquid and the melting heat of the crystals, calculates the content of crystals in the mixture. The content may be shown on a screen or a corresponding signal may be transmitted to a controlling unit, which influences the formation of crystals in the liquid.

2 Claims, 1 Drawing Sheet

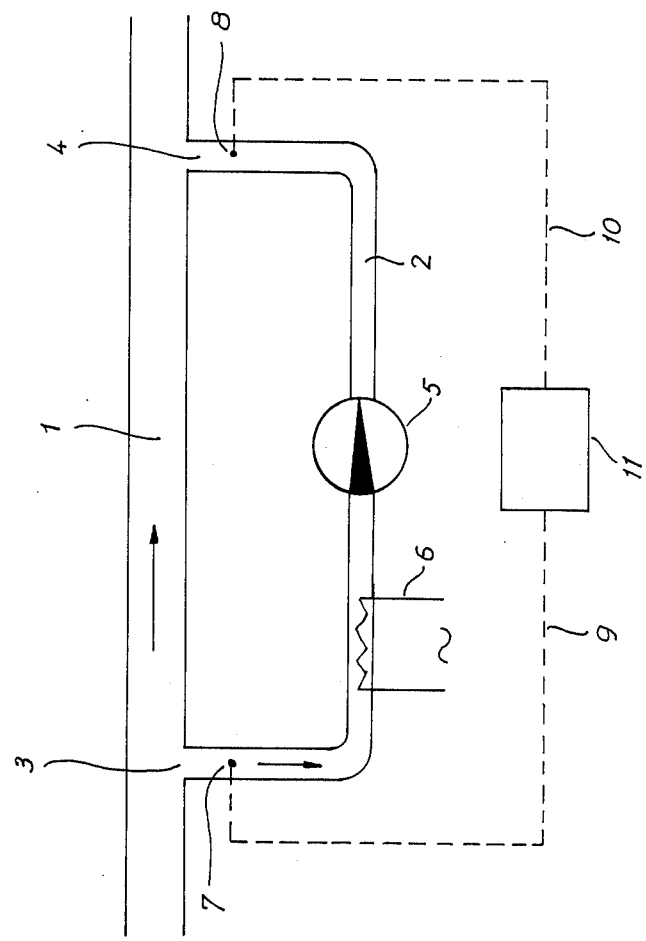

MEASURING THE CONTENT OF CRYSTALS

The present invention relates to a method and an arrangement for measuring the content of crystals in a mixture of liquid and crystals.

In certain industrial processes, as for example methods for freeze stabilization of wine, one needs to have access to a simple, reliable method of measuring the content of ice crystals in a mixture of liquid and crystals. In the Swedish patent application No. 7905962-2 (publication No. 432 776) a method of freeze stabilizing of wine is described. The wine is chilled to a first temperature, at which ice crystals are formed in the wine, but it is still pumpable. The wine is transported to a first storage tank, in which tartrate crystals are formed, and then the wine is heated to a second temperature at which the ice crystals melt, and the formed tartrate crystals are removed from the wine.

In order that this method shall give an optimal result, the operation conditions for the method must be controlled carefully. For this purpose it is important to know the content of ice crystals in the wine, which is pumped to the storage tank. Hitherto one has been forced to use time demanding manual methods for this measurement, for example comprising filling a part of the mixture of liquid, i.e. wine, and ice crystals in a calibrated measuring vessel, which has been heated until all ice crystals have melted, whereupon the change in volume gives a measure of the content of ice crystals.

It is evident, that such a method of measuring is not suitable for adjusting the operation conditions in a process at a factory, if one wishes reasonably short periods in order to obtain steady state. Bearing in mind that different wines have different crystallization properties etc., the demand for a simple method of measuring is more clear. There exists moreover other fabrication processes with systems of liquid/crystals of a completely different type, for example liquid fat/fat crystals, where there exits a demand for a simple, reliable method for measuring the content of crystals in mixtures of liquid and crystals.

The object of the invention is to achieve such a method.

According to the invention a method of the kind described in the introductory part is characterized in the combination of the following steps:

(a) the mixture is forced to stream in a flow with a constant velocity;
(b) to the flow there is added an amount of heat, which is sufficient to melt all crystals in the same;
(c) the temperature difference in the flow before and after the steps (a)-(b) is measured after that all crystals hve melted and the flow has a homogeneous temperature;
(d) with the guidance of information from steps (a), (b) and (c) regarding the velocity of the flow, the amount of heat added to the same, the temperature difference in the flow and known figures about the specific heat of the liquid and the melting heat of the crystals, the content of crystals in the mixture is calculated.

The method and an arrangement for carrying through the same are described in the following with reference to the attached figure, which schematically shows an example of an arrangement for carrying through the method.

In the FIGURE there is a pipe line 1, in which a mixture of liquid and crystals streams. From this pipe line a by-pass line issues, with an inlet 3 and an outlet 4, which also may be the inlet to the pipe line 1, as is shown in the figure. In the by-pass line 2 there is arranged a positive pump 5, i.e. a pump which achieves a constant flow. Of course it is also possible to connect a similar by-pass line 2 to a container, in which a mixture of a liquid and crystals are kept homogeneous by mixing, but the shown example ought to be a more conventional arrangement. An electrical resistance wire 6 is arranged in the by-pass line 2, in such a way that a variable electrical effect can be transmitted to the partial flow, which is pumped through the by-pass line 2. Also the pump 5 adds a certain, limited amount of heat to the flow. Sensing means 7 and 8 for measuring the temperatures $t_1$ and $t_2$ are arranged at the inlet 3 and outlet 4 of the by-pass line. These sensing means 7 and 8 are connected to a unit 11 by way of lines 9 and 10, which unit is arranged to indicate the content of crystals in the mixture with guidance of information brought to the unit about the velocity of the flow, the added amount of heat, the specific heat of the liquid, the melting heat of the crystals and the measured temperature difference.

The arrangement works in such a way, that the pump 5 is adjusted to a suitable constant flow, which corresponds to a part of the flow in the pipe line 1. By means of the resistance wire 6 electrical heat is provided, which is sufficient to melt all crystals in the flow through the by-pass line 2. Also the pump 5 adds a certain, small amount of heat to the flow. The pump 5 should be placed as is shown in the figure, i.e. after the wire 6, in such a way that the flow which is heated is mixed by the pump to a homogeneous liquid with the same temperature before measuring the temperature. The distance between the pump 5 and the sensing means 8 should be so long, that a complete equilibrium of temperature has time to accomodate in the flow. The total amount of heat added to the flow is suitably measured by pumping a flow free from crystals through the by-pass line and measuring the temperature difference $t_2 - t_1$. With the aid of knowledge about the flow G (kg/sec.) and specific heat of the flow $C_1$ (J/kg°C.) the added amount E (W) is easily counted. With knowledge of the melting heat $L_s$(J/kg) of the crystals the following connection is obtained, where X denotes the content of crystals in the flow G:

$$E = X \cdot L_s \cdot G + C_1 \cdot G(t_2 - t_1)$$

$$X = \frac{E - C_1 \cdot G(t_2 - t_1)}{L_s \cdot G}$$

As may be seen X is a linear function of the temperature difference $t_2 - t_1$.

In an example wine with $C_1 = 4.52$ J/g°C. $= 4.52 \cdot 10^3$ J/kg°C. and $L_s = 333 \cdot 10^3$ J/kg was freeze stabilized. By measuring $t_2 - t_1$ in wine free from crystals in a plant according to the figure it was known that 185 W was added to a flow which was measured to 20.0 kg/h $= 5.56 \cdot 10^{-3}$ kg/s. The temperature difference $t_2 - t_1$ in an equally large flow of wine, which comprised a share of crystals and to which was added the same amount of heat, was measured to be 3.68° C. From this known information the content of crystals in the wine was measured to $$X = \frac{185 - 4.52 \cdot 10^3 \cdot 5.56 \cdot 10^{-3} \cdot 3.68}{333 \cdot 10^3 \cdot 5.56 \cdot 10^{-3}} = 0.05$$

i.e. 5%.

This calculation was performed through by the unit 11, which is arranged to store information about the flow G, the specific heat $C_1$ of the liquid, the melting heat $L_s$ of the crystals and the amount of heat added to the flow, whereupon the unit with the help of electrical impulses obtained from the sensing means 7 and 8, which corresponds to the temperature difference $t_2 - t_1$, directly indicates the content of crystals in the mixture on a screen. It is also possible that the unit in some way gives a signal to a controlling unit, which influences the amount of crystals formed in the mixture in a process, which comprises the formation of a desired content of crystals in the liquid.

We claim:

1. A method for measuring the content of crystals in a mixture of liquid and crystals, comprising the steps of:
   (a) bringing the mixture to form a stream having a constant velocity;
   (b) adding an amount of heat to the stream which is at least sufficient to melt all crystals in the stream;
   (c) measuring the temperature in the stream upstream of the addition of the heat ($t_1$) and downstream of the addition of the heat ($t_2$) after all crystals have melted and the stream has achieved a homogeneous temperature; and
   (d) having the knowledge of the information from the previous steps regarding the constant velocity of the stream, the amount of heat added to the stream, the temperature measurements of the stream and knowing the specific heat constant of the liquid and the heat of melting of the crystals, calculating the content of crystals in the mixture, according to the formula $$X = \frac{E - (C_1)(G)(t_2 - t_1)}{(L_s)(G)}$$

wherein X is the content of crystals in the mixture, E is the amount of heat added to the stream, $C_1$ is the specific heat constant of the liquid, G is the constant velocity of the stream, $L_s$ is the heat of melting constant of the crystals, and ($t_2 - t_1$) is the temperature difference in the stream.

2. An apparatus for measuring the content of crystals in a mixture of liquid and crystals comprising a pipe line, a pump for bringing the mixture to form a stream having a constant velocity through the pipe line, heating means for transmitting an amount of heat to the stream, temperature sensing means arranged upstream and downstream of the heating means to measure the temperature of the stream as it arrives at the pipe line ($t_1$) and as it leaves the pipe line ($t_2$) and means for calculating the content of crystals in the mixture once having knowledge of the velocity of the stream, of the added amount of heat, of the specific heat constant of the liquid, of the heat of melting of the crystals and of the temperature measurements of the stream, according to the formula $$X = \frac{E - (C_1)(G)(t_2 - t_1)}{(L_s)(G)}$$

wherein X is the content of crystals in the mixture, E is the amount of heat added to the stream, $C_1$ is the specific heat constant of the liquid, G is the constant velocity of the stream, $L_s$ is the heat of melting constant of the crystals, and ($t_2 - t_1$) is the temperature difference in the stream.

* * * * *